United States Patent
Molony et al.

(10) Patent No.: US 12,136,492 B2
(45) Date of Patent: Nov. 5, 2024

(54) MACHINE LEARNING SYSTEMS AND METHODS TO DIAGNOSE RARE DISEASES

(71) Applicant: Sanofi, Paris (FR)

(72) Inventors: Cliona Marie Molony, Boston, MA (US); Alexandra Dumitriu, Boston, MA (US)

(73) Assignee: Sanofi, Paris (FR)

( * ) Notice: Subject to any disclaimer, the term of this patent is extended or adjusted under 35 U.S.C. 154(b) by 257 days.

(21) Appl. No.: 17/448,507

(22) Filed: Sep. 22, 2021

(65) Prior Publication Data

US 2022/0093252 A1     Mar. 24, 2022

Related U.S. Application Data

(60) Provisional application No. 63/082,370, filed on Sep. 23, 2020, provisional application No. 63/082,369, filed on Sep. 23, 2020.

(30) Foreign Application Priority Data

Dec. 8, 2020  (EP) ..................................... 20315486
Sep. 15, 2021 (EP) ..................................... 21315160

(51) Int. Cl.
*G16H 50/20*         (2018.01)
*G06N 5/022*         (2023.01)
(Continued)

(52) U.S. Cl.
CPC ............. *G16H 50/20* (2018.01); *G06N 5/022* (2013.01); *G16H 10/60* (2018.01); *G16H 50/70* (2018.01); *G16H 70/60* (2018.01); *G06F 40/279* (2020.01)

(58) Field of Classification Search
None
See application file for complete search history.

(56) References Cited

U.S. PATENT DOCUMENTS

2004/0103001 A1   5/2004  Mazar et al.
2015/0112607 A1   4/2015  Meijer
(Continued)

FOREIGN PATENT DOCUMENTS

EP       2357582 A1     8/2011

OTHER PUBLICATIONS

Spiga O, Cicaloni V, Dimitri GM, Pettini F, Braconi D, Bernini A, Santucci A. Machine learning application for patient stratification and phenotype/genotype investigation in a rare disease. Brief Bioinform. Sep. 2, 2021;22(5):bbaa434. doi: 10.1093/bib/bbaa434. PMID: 33538294. (Year: 2020).*

(Continued)

*Primary Examiner* — Katherine Kolosowski-Gager
(74) *Attorney, Agent, or Firm* — Fish & Richardson P.C.

(57) ABSTRACT

A machine-learned model to diagnose patients with a rare disease based on medical data/records, and methods of training such a model are disclosed. A computer implemented method is disclosed for generating a training dataset for training a machine-learning model to identify individuals with a rare disease. the method comprises: generating, from medical literature associated with the rare disease and using natural language processing, an embedding vector for each of a plurality of terms associated with the rare disease; receiving an initial dataset comprising medical data relating to a plurality of individuals with the rare disease; combining the initial dataset with a control dataset comprising a plurality of individuals without the rare disease; and generating, for each individual in the combined dataset, an embedding vector representing the individual based on features associated with the individual and the embedding vectors for the plurality of terms associated with the rare disease.

20 Claims, 8 Drawing Sheets

(51) Int. Cl.
  *G16H 10/60* (2018.01)
  *G16H 50/70* (2018.01)
  *G16H 70/60* (2018.01)
  *G06F 40/279* (2020.01)

(56) References Cited

U.S. PATENT DOCUMENTS

| | | | |
|---|---|---|---|
| 2017/0196541 | A1 | 7/2017 | Boon |
| 2017/0227528 | A1 | 8/2017 | Feng et al. |
| 2017/0228507 | A1 | 8/2017 | Bottinger et al. |
| 2019/0108912 | A1 | 4/2019 | Spurlock, III et al. |
| 2020/0104648 | A1* | 4/2020 | Yadav .................. G06F 18/2433 |
| 2020/0118691 | A1 | 4/2020 | Kiljanek |
| 2021/0104330 | A1 | 4/2021 | Neumann |
| 2021/0327594 | A1* | 10/2021 | Shukla .................. G06N 5/047 |
| 2021/0343414 | A1* | 11/2021 | Robinson ............... G16H 50/30 |
| 2022/0076828 | A1* | 3/2022 | Zhang .................... G06F 40/30 |
| 2022/0093255 | A1 | 3/2022 | Molony et al. |
| 2022/0114273 | A1 | 4/2022 | Njemanze |
| 2022/0223293 | A1* | 7/2022 | Steinberg-Koch ....... G06N 3/08 |
| 2022/0399115 | A1 | 12/2022 | Alter |
| 2023/0248998 | A1 | 8/2023 | Natarajan et al. |

OTHER PUBLICATIONS

Schaefer, J., Lehne, M., Schepers, J. et al. The use of machine learning in rare diseases: a scoping review. Orphanet J Rare Dis 15, 145 (2020). https://doi.org/10.1186/s13023-020-01424-6 (Year: 2020).*

Colbaugh et al., "Learning to Identify Rare Disease Patients from Electronic Health Records," AMIA Annual Symposium Proceedings Archive, Dec. 2018, 2018: 340-347.

Ke et al., "LightGBM: A Highly Efficient Gradient Boosting Decision Tree," Advances in Neural Information Processing Systems 30 (NIPS 2017), 2017, pp. 3146-3154.

Mikolov et al., "Distributed Representations of Words and Phrases and their Compositionality," Adv. Neural Inf. Process. Syst, 2013, vol. 26, 9 pages.

U.S. Appl. No. 17/482,810, filed Sep. 23, 2021, Cliona Marie Molony.

Colbaugh et al., "Robust Ensemble Learning to Identify Rare Disease Patients from Electronic Health Records," Engineering in Medicine and Biology Society (EMBC), 2013 34th Annual International Conference of the IEEE, Jul. 1, 2018, 2018:4085-4088.

International Preliminary Report on Patentability in International Appln. No. PCT/EP2021/076213, mailed on Apr. 6, 2023, 10 pages.

International Preliminary Report on Patentability in International Appln. No. PCT/EP2021/076214, mailed on Apr. 6, 2023, 9 pages.

International Search Report and Written Opinion in International Appln. No. PCT/EP2021/076213, mailed on Jul. 8, 2022, 13 pages.

International Search Report and Written Opinion in International Appln. No. PCT/EP2021/076214, mailed on Jan. 25, 2022, 10 pages.

Koleck et al., "Natural language processing of symptoms documented in free-text narratives of electronic health records: a systematic review," Journal of the American Medical Informatics Association, Apr. 1, 2019, 26(4):364-379.

Wikipedia.com [online], "Hierarchical clustering," Aug. 18, 2020, retrieved on Oct. 4, 2020, retrieved from URL <https://en.wikipedia.org/w/index.php?title+Hierarchical_clustering&oldid=973740550>, 8 pages.

Mekel-Modiano et al., "Symptoms, Cluster Symptoms and Quality of Life among Breast Cancer Survivors Compared to Healthy Women," European Journal of Cancer, Mar. 2012, 4 pages (Abstract only).

* cited by examiner

MACHINE LEARNING SYSTEMS AND METHODS TO DIAGNOSE RARE DISEASES

CROSS REFERENCE TO RELATED APPLICATIONS

The present application claims priority to European Patent Application No. 21315160.8, filed on Sep. 15, 2021, European Patent Application No. 20315486.9, filed on Dec. 8, 2020, U.S. Patent Application No. 63/082,370, filed on Sep. 23, 2020, and U.S. Patent Application No. 63/082,369, filed on Sep. 23, 2020, the disclosures of which are incorporated herein by reference.

TECHNICAL FIELD

This specification relates to the use of a machine-learned model to diagnose patients with a rare disease based on medical data/records, and methods of training such a model.

BACKGROUND

It is estimated that around 300 million people worldwide suffer from a rare disease. Rare diseases typically take longer to diagnose than more common diseases, with the average diagnosis time for a rare disease being over four years. This can lead to significant delays in treating the rare disease and a decrease in the likelihood of successfully treating the rare disease. Many factors contribute to this delay, including unfamiliarity with the rare disease by medical practitioners, a diversity of symptoms for a given rare disease and masking of the disease by symptoms of more common diseases. While traditional diagnostic algorithms can sometimes be effective, they rely on health care provider's (HCP's) awareness, and require verifying numerous clinical characteristics, including differential diagnoses. Such conditions are rarely met in the real world.

SUMMARY

According to a first aspect of this specification, there is described a computer implemented method of generating a training dataset for training a machine-learning model to identify individuals with a rare disease, the method comprising: generating, from a corpus of medical literature associated with the rare disease and using natural language processing, an embedding vector for each of a plurality of terms associated with the rare disease; receiving an initial dataset comprising medical data relating to a plurality of individuals with the rare disease, the medical data for each individual comprising data indicative of a plurality of features of the rare disease experienced by said individual; combining the initial dataset with a control dataset comprising a plurality of individuals without the rare disease to generate the training dataset; and generating, for each individual in the training dataset, an embedding vector representing the individual based on features associated with the individual and the embedding vectors for the plurality of terms associated with the rare disease.

Generating the embedding vector representing an individual may comprise: identifying one or more embedding vectors for terms associated with rare disease that correspond to features of the rare disease experienced by the individual; and averaging the identified embedding vectors for terms associated with rare disease to generate the embedding vector representing the individual.

Generating an embedding vector for each of a plurality of terms associated with the rare disease may comprise: generating, using a natural language processing algorithm, an embedding vector for each of a plurality of terms in the corpus of medical literature; comparing the embedding vector for each of the plurality of terms in the corpus of medical literature to embedding vectors of one or more predefined terms known to be associated with the rare disease using a distance metric; and discarding an embedding vector for a term in the corpus of medical literature if a distance between said embedding vector and an embedding vector of a predefined term known to be associated with the rare disease is greater than a threshold value.

The method may further comprise identifying a plurality of clusters of individuals in the initial dataset using an unsupervised clustering method; identifying one or more of the clusters as being least representative of the rare disease based on the medical data of the individuals in the clusters; and removing, prior to combining the initial dataset with the control dataset, one or more of the individuals from the one or more clusters identified as being least representative based on the medical data of said one or more individuals.

Identifying one or more of clusters as being least representative of the rare disease may comprise: identifying a representative symptom of the rare disease for each of the plurality of clusters; comparing the represented symptom for each cluster to a predefined set of known symptoms of the rare disease, the predefined set of known symptoms comprising a set of more representative symptoms and a set of least representative symptoms; and identifying a cluster as being least representative of the rare disease if the representative symptom of the cluster is in the set of least representative symptoms.

Removing one or more of the individuals from one or more clusters identified as being least representative may comprise: for each individual in the clusters identified as being least representative: determining whether medical data associated with the individual satisfies a threshold condition, the threshold condition based on symptoms of the rare disease; and removing the individual from the identified clusters if the threshold condition is not satisfied.

Identifying a plurality of clusters of individuals in the initial dataset may comprise using a hierarchical agglomerative clustering to cluster the dataset into a predetermined number of clusters.

The method may further comprise: comparing medical data associated with individuals in the initial dataset to medical data associated with individuals in the control dataset to identify one or more potential symptoms of the rare disease; and augmenting the training dataset with the one or more potential symptoms of the rare disease.

The control dataset may comprise individuals without the rare disease having at least a threshold number of symptoms of the rare disease.

Combining the initial dataset with a control dataset may comprise matching a plurality of individuals in the control dataset to each individual in the initial dataset at a predefined ratio. The matching may be based on one or more demographic properties of the individuals.

According to a further aspect of this specification, there is disclosed a computer implemented method of training a machine-learned model to classify an individual as having a rare disease based on medical records of the individual, the method comprising using a supervised learning technique to train the machine-learned model using a labelled training dataset, wherein the training dataset has been generated using any of the methods described herein for generating a training datset, and wherein the machine learning model takes as input data comprising the embedding vector representing an individual.

The machine-learning model may be trained on a subset of data in the labelled dataset, the subset comprising, for each individual in the dataset with the rare disease, medical data collected prior to the individual being diagnosed with the rare disease.

According to a further aspect of this specification, there is disclosed a computer implemented method of diagnosing a disease, the method comprising: inputting, into a machine learned model, medical data associated with an individual, the medical data comprising an embedding vector representing the individual that is based on features associated with the individual; processing, using the machine learned model, the input medical data to generate data indicative of whether the individual associated with the medical data as the disease; and outputting, from the machine learned model, the data indicative of whether the individual associated with the medical data has the disease, wherein the machine learned model has been trained using any of the training methods described herein.

According to a further aspect of this specification, there is disclosed a system comprising one or more processors and a memory, the memory comprising computer readable code that, when executed by the one or more processors, causes the system to perform any of the methods described herein.

According to a further aspect of this specification, there is disclosed a computer program product comprising computer readable code that, when executed by computing apparatus, causes the computing apparatus to perform a method according to any of the methods described herein.

As used herein, the term "rare disease" means a disease that affects a substantially low number of people, e.g., less than 1 in 2000 people, within the general population. Currently, there are over 6,000 known rare diseases, and new rare diseases are being discovered all the time. In the following written description, example methods will be described in relation to Gaucher's disease, though it will be appreciated that the methods are equally applicable to other rare diseases.

DETAILED DESCRIPTION

This specification describes methods of training a machine-learned model to identify patients (also referred to herein as individuals) at risk of having a rare disease. The machine learning system uses a symptomatic approach to identify individuals at risk of rare diseases. The system is trained using Electronic Medical Records for a substantial number of patients. The trained model may be used, based on an individual's symptoms/electronic medical records, to determine if the individual has a particular rare disease or is at risk of having a particular rare disease. This can allow patients with a rare disease to be identified and captured earlier in the disease progression, allowing them to obtain access to effective treatment and avoid unjustified morbidity and burden.

Due to the low rate of individuals with a rare disease in the general population, datasets that can be used in training machine-learned models to diagnose the rare disease are often noisy and/or unbalanced. This specification describes methods of generating a reduced noise and/or balanced dataset that, when used to train a machine-learned model, results in a more accurate model (i.e. a model with fewer false positives and/or false negatives).

Figure 1:
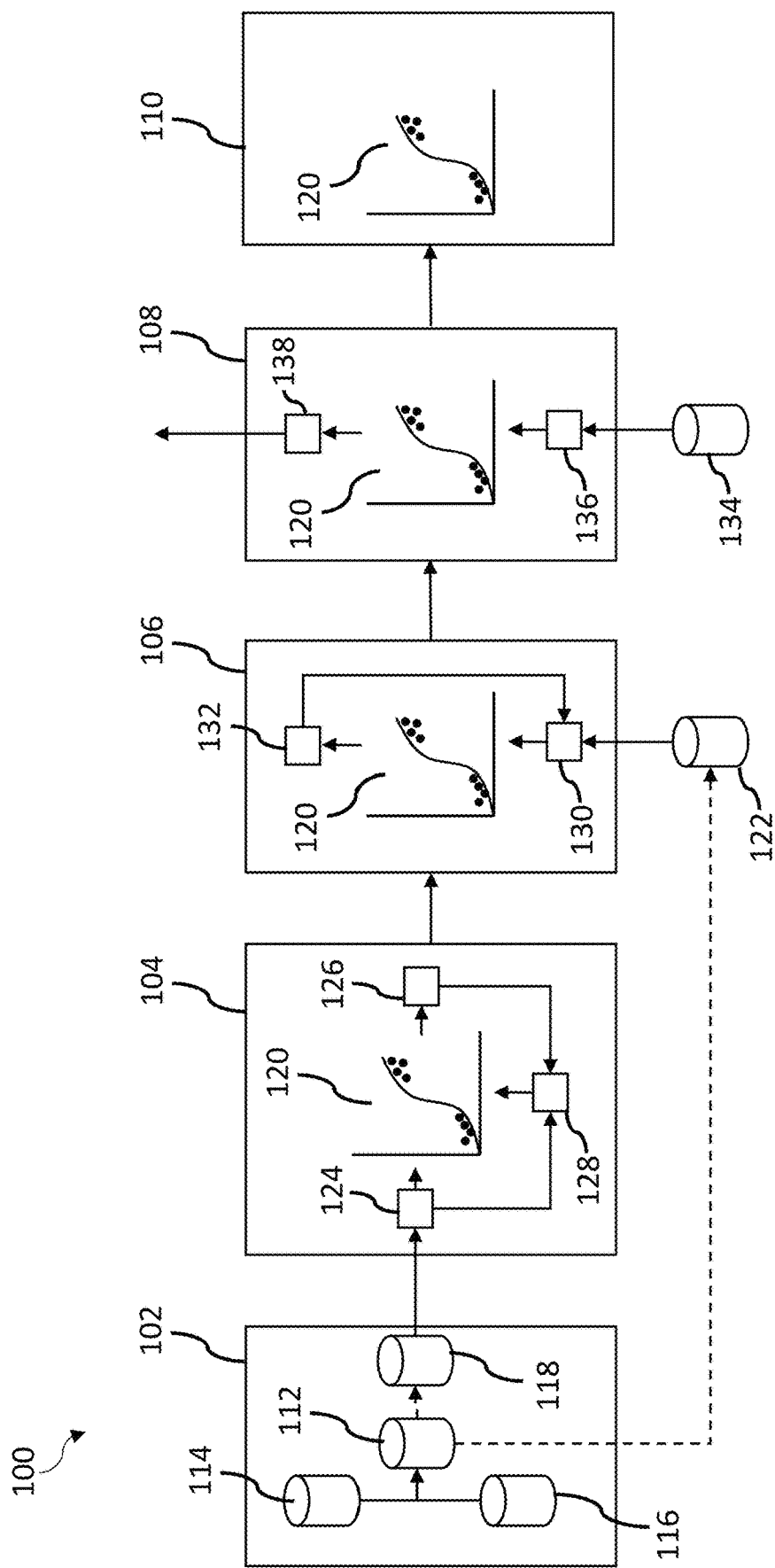
FIG. 1 shows an overview of an example pipeline for training a machine-learned model to identify individuals with a rare disease.

FIG. 1 shows an overview of an example pipeline 100 for training a machine-learned model to identify individuals with a rare disease. The method 100 may be performed by a computer. Each of the operations 102-110 of the pipeline 100 may be performed independently or in combination with any one or more of the other operations.

The pipeline 100 comprises a dataset generation operation 102, a model training operation 104, a model testing operation 106, a model verification operation 108, and a model output operation 110.

During the dataset generation operation 102, a training dataset 112 is generated by combining a target dataset 114 comprising medical data of a plurality of individuals with the rare disease, and a control dataset 116 comprising medical data of a plurality of individuals without the disease 116. Each individual in the training dataset 112 is associated with a binary label indicative of whether said individual has the rare disease or not. Methods of generating the training dataset are described in more detail below with reference to FIG. 2.

The medical data for each individual comprises one or more symptoms experienced by the individual. The symptoms comprise known symptoms of the rare disease and may additionally comprise other symptoms (or combinations of symptoms) that may not be as clearly linked to the rare disease. For a given individual, the medical data may comprise all symptoms experienced by the individual that have been recorded. The medical data may comprise medical procedures and conditions associated with the individual (e.g. indications, treatments, comorbidities). The medical data may comprise one or more of: physiological data; vital sign data (e.g. BMI, blood pressure, pain scores); lab values (e.g. A1C, eGFR, FEV); biomarkers; medications received by the individual; and/or individual details (e.g. age, gender, smoking status, ethnicity). In some embodiments, each individual is represented in the training dataset by an embedding vector that is based on a natural language embedding of features in the medical data associated with the individual.

In some embodiments, data on the interactions of an individual with healthcare providers may also be included in the medical data for each individual. The interactions may comprise one or more of: visits (i.e. the type of visit to a healthcare provider, e.g. emergency, inpatient, outpatient etc.); encounters (i.e. interaction types that the patient has had, e.g. home visits, imaging etc.); and/or providers (i.e. the type of healthcare professional seen by the patient, e.g. neurologist, cardiologist etc.). The interactions may be encoded with a binary flag depending on whether or not the individual has had that interaction type. Alternatively or additionally, a frequency of the interactions may be provided. Alternatively or additionally, a date of the first occurrence of that interaction for the individual may be provided.

The medical data may further comprise demographic data, such as location, gender and/or ethnicity.

Other examples of medical data that may be used will be familiar to the skilled person.

In some embodiments, symptoms associated with each individual are associated with an age of the first occurrence of the symptom in that individual. This can allow correlations between symptoms and age to be accounted for by the machine-learned model 120. Such an association can assist in training the machine-learned model 120 to detect early onset symptoms. A machine-learned model 120 trained on such data may favour symptoms that have different onset ages between control and rare disease patients, and may favour early onset/younger patients. Alternatively or additionally, symptoms may be flagged with a binary presence/absence. A machine-learned model 120 trained on such data may favour symptoms that have a different prevalence between control and rare disease patients, and may favour an accumulation of comorbidities in patients/older patients.

Once generated, the training dataset 112 may be divided into a first dataset 118 (also referred to herein as the "learning dataset") that is used to train a machine-learned model 120, and a second dataset 122 (also referred to herein as a "test dataset") that is used to test the machine-learned model 120 once it has been trained. During the model training operation 104, supervised machine-learning techniques are used to train a machine-learned model 120 (herein also referred to as a "model") on the learning dataset 118 to classify an individual as either having or not having the rare disease based on medical data associated with said individual input to the model 120. Input data 124 comprising medical data associated with an individual in the first dataset 118 is input into the model 120, which processes the input data to generate a proposed classification 126 for that individual, the proposed classification 126 is indicative of whether the model classifies the individual as having the rare disease or not having the rare disease. The proposed classification 126 is output by the model 120 and compared the input data 124 to a known classification in order to determine updates 128 to parameters of the model 120. This comparison may, for example, be performed using a loss/objective function, with a training goal of optimising said loss/objective function. The loss function may be a classification loss, such as a cross-entropy loss. This process is iterated over the training data until a threshold condition is met, e.g. a threshold number of training epochs.

The machine-learned model 120 may be any type of trainable model that can be used for classification. For example, the model may include a logistic regression model. The logistic regression model may have a Lasso penalisation term. Lasso penalisation applies a penalisation on some parameters/coefficients of the model that don't bring signal to the model. Lasso penalization allows the removal of features from the model 120 that do not carry any signal, as well as providing interpretability of parameters/coefficients of the model 120: the bigger the coefficients is, the more important the variable is. The logistic regression may have a shrinkage parameter of between 0.2 and 3. An exponential increment may be used for a threshold number of values, e.g. 10 values.

The model 120 may include a Light Gradient Boosting Model (LGBM). A LGBM seeks to improve the prediction power by training a sequence of weak models (for example decision trees), each compensating the weaknesses of its predecessors. Use of a LGBM allows for feature selection (e.g. via trees), works well with a high number of features, and takes into account groups of symptoms. The LGBM model may, for example, have a maximum depth of between 10 and 40, for example 10, 20 or 30. A minimum child weight of between 0.05 and 0.25 may be used, e.g. between 0.1 and 0.2. The number of child leaves may be between 10 and 40, e.g. 10, 20 or 30. The number of estimators (trees) may be between 50 and 350, such as 100, 200 or 300. An example of a LGBM is described in "*LightGBM: A Highly Efficient Gradient Boosting Decision Tree*" (Ke, G. et al., 2017, Advances in Neural Information Processing Systems 30, Eds Curran Associates, Inc, pp. 3146-3154).

It will be recognised by the skilled person that other types of machine-learned models 120 may be used, e.g. the model 120 may include a neural network, such as a recurrent neural network (RNN), or a support vector machine. RNNs can outperform other models in patient identification tasks on EHR data and may require less pre-processing than traditional methods. For rare diseases, they may be able to capture useful temporal patterns such as meaningful repetition of symptoms, simultaneous occurrence of symptoms, specific succession of visits to medical specialists.

In some embodiments, a plurality of different machine-learned models are trained, and the best performing model is selected using the average area under the precision recall curve (AUPRC). The plurality of models may comprise models of different types, and/or models of the same type with different hyper-parameters.

In some implementations, K-fold cross validation or bootstrap sampling may be used to limit sample bias and improve the stability of obtained models. In other words, cross validation is performed X times, by selecting each time Y control patients for 1 GD patient from the training dataset. Within each bootstrap, control patients are unique (i.e. no replacement). Control patients can be selected in several bootstraps (i.e. selection with replacement between bootstraps). In some embodiments, the training data is initially composed of Z control patients for 1 patient with Gaucher's disease ("GD"), where Y<Z. In some embodiments, X is ten, though other values may be used. In some implementations, Y=X. A control patient is a patient who does not have the rare disease or has not been diagnosed as having the rare disease.

A good candidate model for identification of the rare disease should be expected to: output a continuous probability while trained on a binary target; take age encoding of features into account; work well with a mixture of binary and numerical features; and/or do not have necessarily an additive sensibility to the presence of characteristics (e.g., higher weight when multiple symptoms are present).

The distribution of the top (e.g., 10 best) AUPRCs (one for each bootstrap) may be analysed to ensure the robustness of the algorithm. The final algorithm may be a randomly picked bootstrap among the top (e.g., 10) choices, i.e., a train dataset at a 1 GD for 10 control ratio and its associated best hyper-parameters determined with the cross-validation.

In some implementations, a subset of the medical data for one or more individuals in the training dataset 112 is used to train 104 and/or to evaluate 106 the model. The subset of medical data may exclude any symptoms of the rare disease identified and/or medical data collected after the diagnosis of the individual with the rare disease, i.e. include only symptoms and/or medical data taken before the date of diagnosis of the rare disease. In some embodiments, the subset of medical data only includes symptoms of the rare disease identified and/or medical data collected prior to some predefined time before diagnosis of the individual with the rare disease. For example, only data prior to a predefined number of consultations before the diagnosis may be used (e.g. one or two consultations prior to diagnosis). For individuals without the rare disease, all medical data may be used.

Following training operation 104, the performance of the model 120 may be evaluated on the second (test) dataset 122 during a testing operation 106. Input data 130 comprising medical data associated with an individual in the first dataset 122 is input into the model 120. The model processes the input data to generate a proposed classification 132 of the input data. The proposed classification for each individual in the test dataset 122 is compared to a known classification for that individual, and an accuracy score for the model is determined based on the results. If the model 120 satisfies a threshold accuracy condition on the test dataset 122, then the model 120 is output 110 for use in identifying individuals with the rare disease, for example in a database comparable to/compatible with the one used for training. In some embodiments, the model may alternatively or additionally be output to a verification operation 108. Otherwise, the model 120 may be returned to the training operation 104 for further refinement.

In some implementations, the testing operation 106 may comprise a first testing operation in which the model 120 is applied to the test dataset 122 with no censoring of any event during the observation period, to assess how the model 120 would perform in conditions close to the real-life application. As an example, the model may be assessed using a full electronic health records ("EHR") history of a patient/patients up to the present day. The testing operation 106 may alternatively or additionally include a second testing operation in which events occurring after the index dates (i.e. the date of the rare disease diagnosis) of individuals are censored (i.e. removed from the input to the model). This can assess whether the model would be able to identify rare disease patients with the same amount of information that would be available to a physician prior to diagnosis.

A model verification operation 108 is, in some embodiments, used to assess the real world performance of the trained model 120 in a compatible database (e.g. an independent HER system). A further dataset 134 comprising unlabelled medical data associated with a plurality of individuals that were not in the training dataset is used to assess the performance of the model 120. Input data 136 comprising medical data associated with an individual in the further dataset 134 is input into the model 120, which processes the input data to generate a proposed classification 138 of the input data. The inputs may be selected from a set of individuals in the further dataset 134 that have at least a threshold number of symptoms of the rare disease. For example, the threshold number may be at least two symptoms of the rare disease.

The proposed classification for each individual in the further dataset 134 identified as having the rare disease is evaluated by a medical professional 140 to verify the diagnoses. If the performance of the model satisfies a threshold condition, e.g. if the model accuracy is higher than a threshold value when compared to the assessment of the medical practitioner, the model 120 is outputted 110 for use. Otherwise, the model 120 may be returned to the training operation 104 for further refinement.

Figure 2:
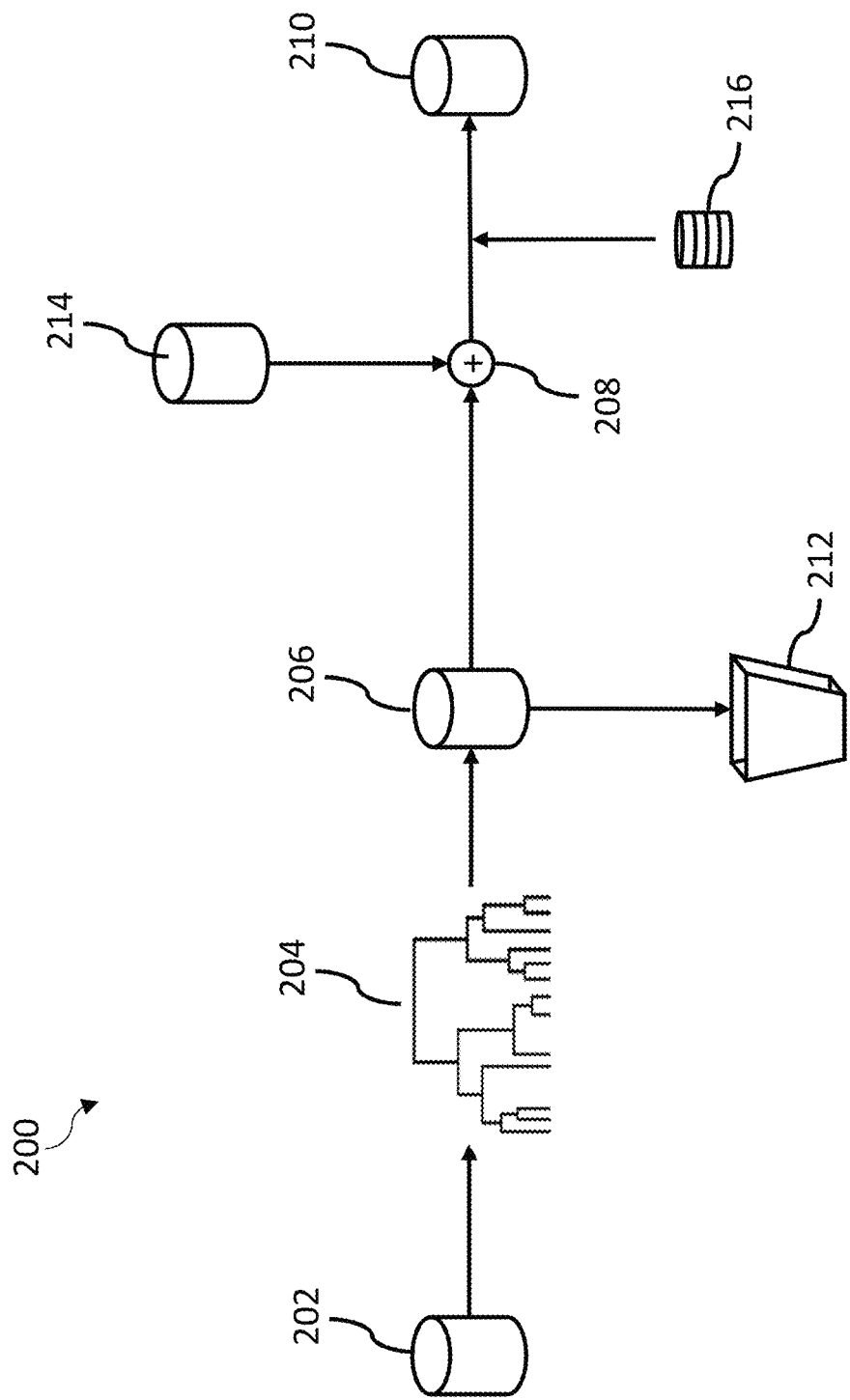
FIG. 2 shows an overview of an example method for generating a training dataset for use in training a machine-learning model to identify individuals with a rare disease.

FIG. 2 shows an overview of an example method 200 of generating a training dataset 210 for use in training a machine-learning model to identify individuals with a rare disease. The method 200 may be performed by a computer. The method corresponds to the dataset generation operation 102 of FIG. 1. The method may operate on a medical database comprising medical data from a plurality of individuals.

The method 200 comprises an initial target dataset creation operation 202, a clustering operation 204, a refinement operation 206 (also referred to herein as "pruning"), and a merging operation 208. The method 200 may, in some embodiments, further comprise an augmentation operation 216 that may be performed either prior to or after the merging operation 208.

During the initial target dataset creation operation 202, a plurality of individuals who have been identified as having a given rare disease and/or who are receiving treatment associated with the rare disease (also referred to herein as "RD individuals") are identified in a medical database. An initial cohort of RD individuals is selected from the plurality of individuals who have been identified as having the rare disease.

One or more acceptance criteria may be applied to identify the plurality of RD individuals. The acceptance criteria may comprise a symptom-based threshold criterion. For example, a plurality of features associated with the rare disease may be identified by reviewing the literature associated with the rare disease, and the one or more of acceptance criteria may comprise having a threshold number of features of the rare disease. The features may comprise a set of symptoms of the rare disease. The set of symptoms may be divided into a plurality of subsets that relate to known subtypes of the rare disease. As an example, in the case of Gaucher's disease, each feature may be associated with one or more of the three sub-types of the disease. A plurality of features are identified as being "representative" features of the disease, i.e. characteristic of the rare disease. One or more of the features may be classified as "least representative" features that are present in individuals with the rare disease, but not in themselves characteristic of the disease, e.g. generic symptoms. The threshold criteria may comprise having a threshold number of the identified disease symptoms. The threshold number may lie between one and four, e.g. at least two of the identified symptoms.

In some embodiments, the acceptance criteria comprise having at least a threshold period of coverage in the medical database, e.g. having at least one year of coverage.

In some embodiments, the acceptance criteria comprises having at least a threshold number of independent diagnoses of the rare disease. The threshold number of independent diagnoses can be at least two. Depending on the rare disease, the threshold number may be higher. Independent diagnoses can include diagnose of the rare disease for an individual by multiple healthcare providers.

As a specific example, a first plurality of individuals who have been diagnosed with the rare disease are identified in the medical dataset. The identified individuals have received at least two diagnoses of the rare disease. A second plurality of individuals receiving a treatment associated with the rare disease, but who have not been diagnosed with the rare disease, are identified. An initial cohort is formed by combining individuals in the first and second plurality of individuals that pass an acceptance criterion, e.g. only individuals that have at least two symptoms of the rare disease are included in the initial cohort.

In some implementations, individuals may be excluded from the initial cohort based on one or more exclusion criteria. The exclusion criteria may include the individual having an incoherent timeline (e.g. a reported first date of activity after an Index-Date; a reported last date of activity before an Index-Date; and/or a date of death before an Index-Date). The exclusion criteria may alternatively or additionally comprise having one or more other diseases, e.g. having another disease of a similar type (which may indicate a misdiagnosis of the rare disease of interest), or affecting similar systems.

An initial target dataset 202 is generated from the medical data for the RD individuals, the initial target dataset 202 comprising, for each RD individual, an indication of which of the features associated with the disease are present in that RD individual. For example, each individual may be associated with a vector of binary labels, each component of the vector indicating the presence or absence of an associated feature of the rare disease. Each RD individual may also be associated with demographic data for that RD individual.

The initial target dataset 202 may, in some embodiments, undergo further processing in the clustering 204 and refinement operations 206 in order to generate a cleaner/more balanced dataset for training a machine-learned model.

During the clustering operation 204, an unsupervised clustering algorithm is applied to the initial target dataset to cluster the RD individuals into a plurality of subsets (also referred to herein as clusters). The data may be clustered into a predetermined number of subsets. The predetermined number of subsets may depend on properties of the rare disease, e.g. be a fraction of the number of symptoms identified, and/or the number of subtypes of the rare disease.

An example of such an unsupervised clustering algorithm is Hierarchical Agglomerative Clustering (HAC), which clusters the data into a predefined number of subsets. HAC consists in regrouping observations from the bottom up. Each individual starts in their own cluster, and clusters are grouped together until the predefined number of subsets is reached A measure of dissimilarity is computed between sets of observations in order to decide which ones will be gathered. The measure of dissimilarity is computed using a metric and a linkage criterion. The metric is used to compute the distance between each observation. The linkage criterion determines the distance between each set of observations. It will be appreciated that other unsupervised clustering algorithms may alternatively be used. In some implementations, p-values between clusters are calculated to assess if clusters could have been obtained by chance.

Once clustered into subsets, characteristic features for each subset/cluster are identified. The characteristic features may be identified based on common symptoms between RD individuals within each subset, e.g. the most common symptom/combination of symptoms within each subset may be identified as the represented feature for that subset. The characteristic feature may alternatively or additionally be based on a symptom type, e.g. all of the individuals in a cluster may have neurological symptoms. The characteristic feature may alternatively or additionally be based on demographic properties of the individuals in the cluster, such as the age of the individuals, e.g. "young patients with symptom X". Many other examples of characteristic features are possible.

Figure 3:
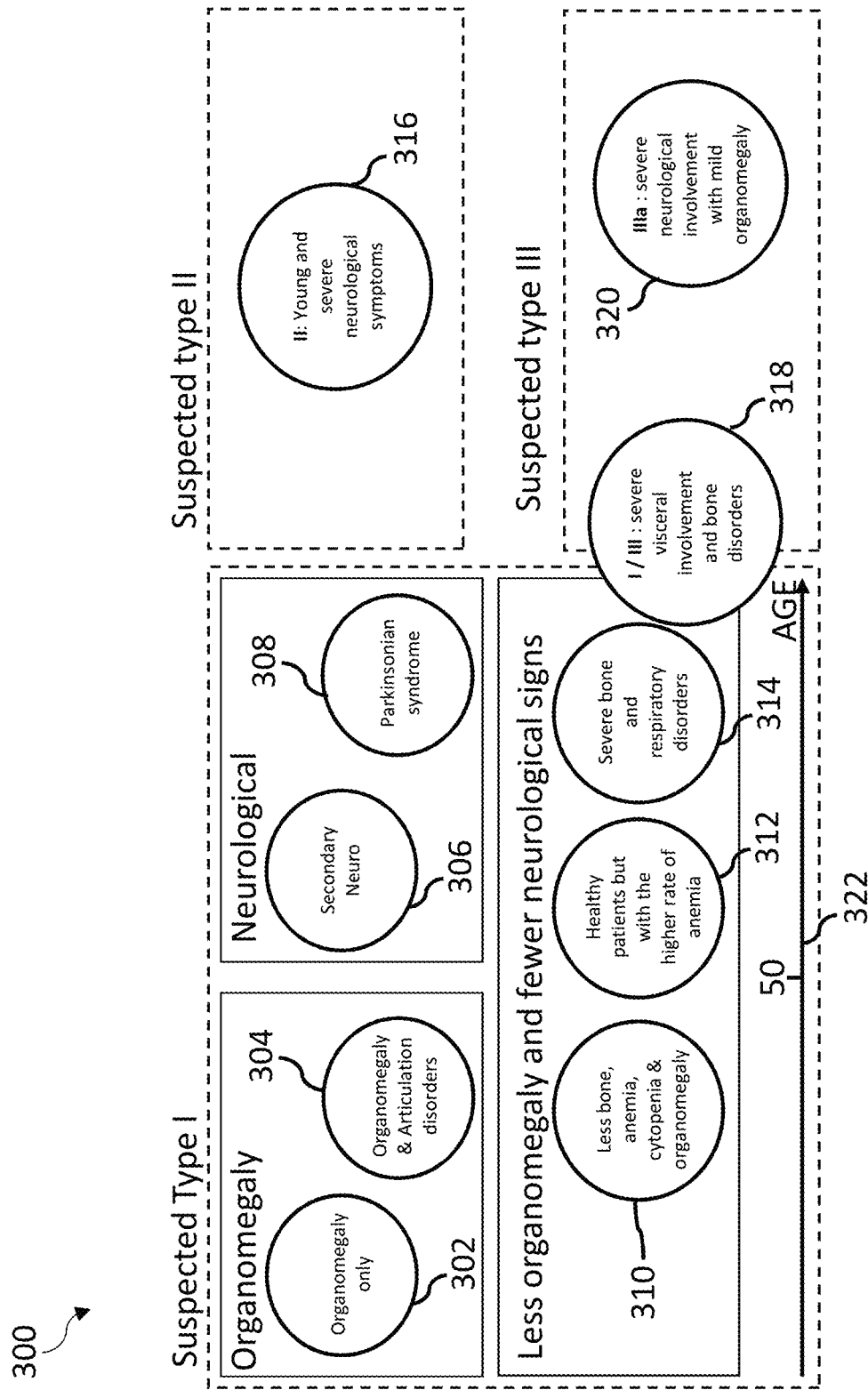
FIG. 3 shows an example of identities of clusters of patients with Gaucher's disease identified by a clustering algorithm.

An example of subsets 300 for Gaucher's disease identified by a clustering algorithm is shown in FIG. 3. In this example, individuals with Gaucher's disease (also referred to herein as "GD individuals") have been clustered into ten clusters/subsets 302-320. Based on properties of the GD individuals in the cluster, each cluster is assignment a characteristic feature. In the example shown, the clusters are labelled based on dominant symptoms/combination of symptoms and/or patient types within the clusters: organomegaly only 302; organomegaly & articulation disorders 304; secondary neurological 306; Parkinsonian syndrome 308; less bone, anaemia, cytopenia & organomegaly 310; healthy patients but with the higher rate of anemia 312; severe bone and respiratory disorders 314; young and severe neurological symptoms 316; severe visceral involvement and bone disorders; and severe neurological involvement with mild organomegaly.

With the exception of the severe visceral involvement and bone disorders cluster, the individuals within each cluster are associated with one of the three types of GD. Type I clusters are also correlated with age 322.

In some embodiments, features identified using the clustering operation 204 may be used as feature labels for the training dataset.

Returning to FIG. 2, following the clustering operation 204, a refinement operation 206 may, in some embodiments, be performed on the initial target dataset to generate a refined dataset (also referred to herein as a "pruned" dataset). During the refinement process, one or more of clusters are identified as being least representative of the rare disease based on the medical data of the RD individuals in the subsets. One or more of the RD individuals from these clusters are then discarded 212 based on the medical data of those individuals, e.g. if the medical data does not satisfy an additional threshold condition. Refining the dataset by removing individuals with a paucity of information in this way can reduce the amount of noise in the dataset, while maintaining enough information to train an accurate model.

Identifying a cluster as least representative of the rare disease may comprise comparing the characteristic features of each cluster to the list of identified features of the disease and identifying clusters whose characteristic feature matches a known least representative feature of the rare disease or a generic feature of the rare disease.

For the clusters identified as least representative of the rare disease, an additional threshold condition is applied to each RD individual in the clusters to determine whether to keep or to discard that RD individual from the training dataset. The additional threshold condition is stricter than the threshold condition used when creating the initial target dataset. RD individuals in the least representative clusters may be removed if they have fewer than a threshold number of symptoms of the rare disease. The threshold number may be higher than the threshold number used in creating the initial cohort. For example, if an individual is included in the initial cohort if they have at least two symptoms of the disease, then individuals in the least representative clusters may be discarded if they have fewer than three symptoms. Alternatively or additionally, the stricter threshold condition may comprise a condition that at least one of the symptoms experienced by the individual is a characteristic symptom, e.g. if the individual only has least representative/generic symptoms, the data associated with that individual is discarded.

Figure 4:
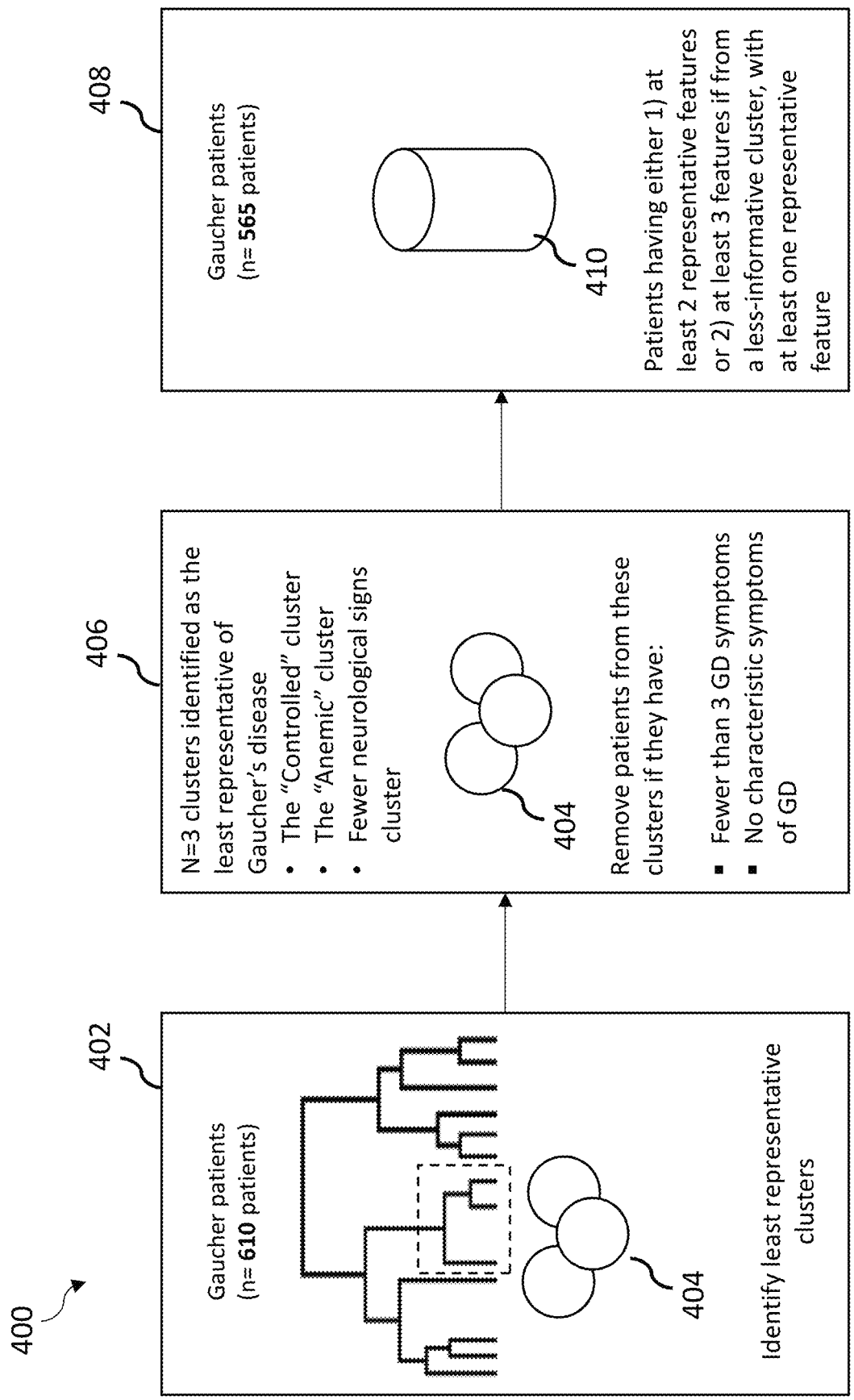
FIG. 4 shows an example of a method of refining a dataset of patients with a rare disease.

An example of a method 400 of refining the clusters for Gaucher's disease of FIG. 3 is shown in FIG. 4. The initial cohort in this example has 610 individuals. The method comprises identifying 402 one or more clusters 404 as being least representative of GD, for example by comparing the characteristic features of the clusters to a list of least representative features of GD. In this example, three clusters from FIG. 3 are identified as being least representative: the "controlled" cluster; the "anaemic" cluster; and the "fewer neurological signs" cluster.

Following identification 402, a threshold condition 406 is applied to the individuals in the identified clusters 404. In this example, an individual is removed from these clusters if that individual has fewer than three GD symptoms or no representative/characteristic symptoms of GD.

A refined dataset 410 of the initial cohort minus the removed individuals is output 408 for further processing. The refined dataset in this example has 565 individuals, i.e. 45 individuals have been removed from the three identified clusters 404. The refined dataset thus has patients that either have (1) two or more representative features of GD; or (2) at least three features of GD, one of which is representative of GD. This limits the number of removed patients while keeping the cohort with enough relevant information to train an algorithm.

Returning to FIG. 2, following the refinement operation 206 or, if the refinement operation is not performed, following the clustering operation 204, a merging operation 208 is performed to create the training dataset 210. During the merging operation, the pruned/refined dataset is merged with a medical data from a control dataset 214 The control dataset comprises medical data from individuals that have not been diagnosed with the rare disease (also referred to herein as "control individuals").

The control individuals are selected from the control dataset based on having at least a threshold number of symptoms of the rare disease. The threshold number may lie between one and five, e.g. the threshold number may be two.

In some embodiments, each individual in the pruned dataset is matched with plurality control individuals at a pre-defined ratio in order to generate a balanced dataset. The predefined ratio may be dependent on the prevalence of the rare disease in the general population. The predefined ratio may be between 5 and 20 control individuals per RD individual, for example 10. The matching may be performed based on one or more demographic properties of the individuals in the pruned dataset. Examples of demographic properties include: age (e.g. in age ranges); gender; and/or data coverage (e.g. the time span data for the individual is available over).

In other words, for each RD individual, a predefined number of control individuals are sampled from the set of control individuals with the same demographic properties as the RD individual. Exact matching without replacement may be used.

Figure 5:
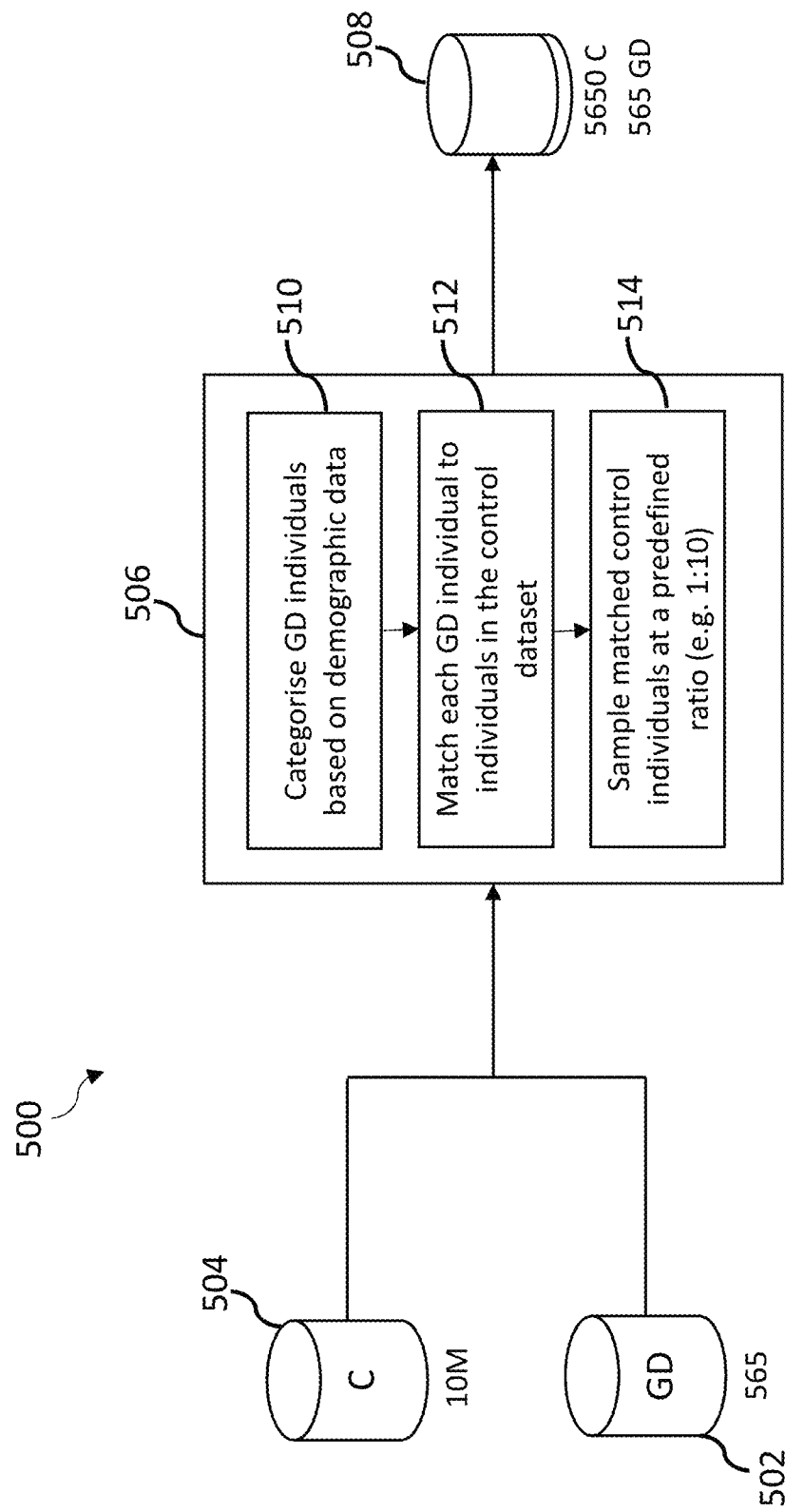
FIG. 5 shows an example of a method of combining a rare disease dataset with a control dataset.

An example of such a matching process 500 for Gaucher's disease is shown in FIG. 5. A pruned dataset 502 of 565 Gaucher's disease patients (GD individuals) is merged 506 with control individuals selected from a dataset 504 of 10 M individuals to create a training dataset 508. In this example, the GD individuals are each categorised 510 into a demographic based on gender (i.e. male or female), an age range they fall within (e.g. 0-10 years, 11-20 years, etc.) and a coverage period (0-1 year, 1-2 years, etc.). For each GD individual, corresponding individuals in control dataset in the same demographic are identified 512 and sampled 514 at a predefined ratio, e.g. 1:10. The result is a training dataset 508 (T) with 565 GD individuals and 5650 control individuals.

Control individuals may be excluded from inclusion in the merged dataset based on one or more further exclusion criteria. The further exclusion criteria may comprise having one or more other diseases, e.g. having another disease of a similar type, or affecting similar systems. The further exclusion criteria may alternatively or additionally comprise having a different coverage period to individuals in the pruned dataset. In some embodiments, a fictitious "control index date" is created for each control individual so that both rare disease and control patients have the same period of data on which the algorithm can learn. The control index date may be set at the median look-back period among the rare disease population, for a given coverage length.

Returning to FIG. 2, in some embodiments, the method 200 further comprises one or more data augmentation operations 216. The data augmentation operations 216 identify additional medical data that may be relevant to the diagnosis of the rare disease, and add this additional medical data to the training dataset 210.

Figure 6:
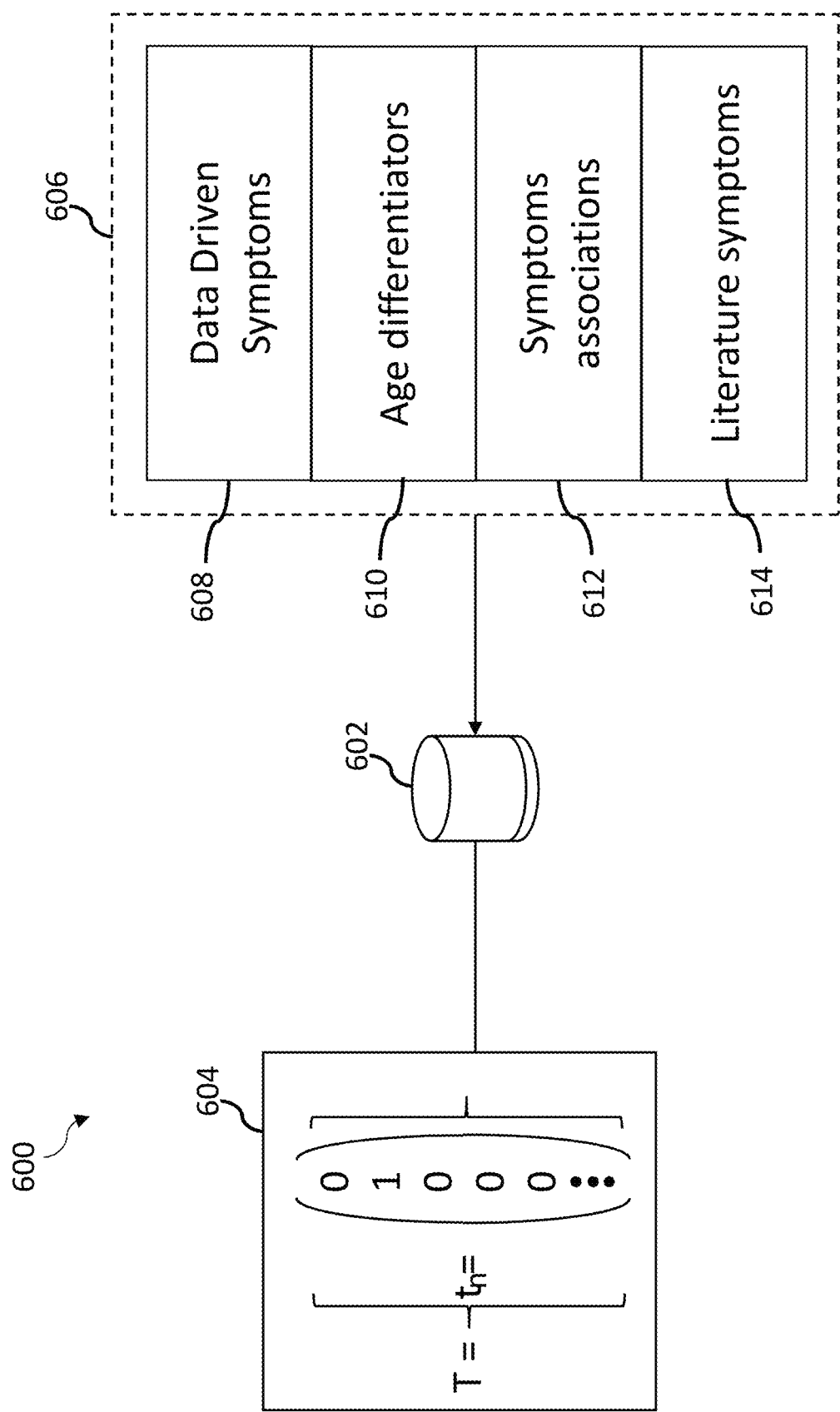
FIG. 6 shows an example of a method of augmenting a training dataset with additional features.

FIG. 6 shows example methods 600 of augmenting the training dataset. Prior to augmentation, each individual in the training dataset 602 is associated with an indication of which symptoms of the rare disease are present in that individual 604. For example, as shown in FIG. 6, a vector of binary labels/flags ($t_n$) may be associated with each individual (n), where each component of the vector corresponds to whether or not that feature is present in the associated individual. In the example of Gaucher's disease, N=69 features are selected from the literature/by GD experts to be components of the vector.

Data augmentation may identify one or more additional features 606 associated with the rare disease in medical data associated with the individual that has not already been included in the training data. These additional features are added to the data associated with individual, for example as additional components to the vector of features associated with that individual, or as additional feature vectors associated with each individual.

In some embodiments, a data-driven augmentation 608 may be used that applies statistical methods to medical data associated with individuals in the control dataset and target dataset in order to identify additional features present in the target dataset at significantly lower frequencies compared with the control dataset (or vice versa). An indication of the presence or absence of these additional features may be added to the data associated with each individual. Data-driven features are a good way to discover new features that are more prevalent within our population of interest. Associated with medical knowledge, they can bring novel evidence. For example, for each feature a Chi-square and Cramér's V test is performed between the rare disease cohort and the control cohort. The Chi-square test indicates if there is a significant relationship between variables. Cramér's V is a number between 0 and 1 that indicates how strongly two variables are associated. The features are ranked according to their Cramér's V score. The decision to select the feature is then based on the highest value of Cramér's V, if the Chi-square test is significant.

For example, in some embodiments, the selected features will be the ones that are not already present, for which the strength of association using Cramér's V coefficient between both cohorts is above a threshold value (e.g. above 0.1) and for which p-values using a Chi-square test are below a threshold value (e.g. below 0.05), to assess sampling bias.

The selected features may be encoded for each individual as a binary flag indicating the presence or absence of that feature in the individual. Alternatively or additionally, the selected features may be encoded for each individual as an age of first occurrence in that individual.

Alternatively or additionally, age differentiators 610 may be identified. One or more correlations between age and symptoms are identified in the data. These can help identify symptoms that probably occur due to the rare disease and not because of aging. A binary variable for each selected symptom is created depending on the age of occurrence, e.g.

whether the symptom occurs before or after the average occurrence in the literature for individuals without the rare disease. The selected symptoms may be symptoms that commonly occur with ageing, such as neurological symptoms (e.g. Parkinsonian symptoms, tremors) and/or bone conditions (e.g. osteoarthritis, osteoporosis).

Alternatively or additionally, symptom associations 612 may be identified. Symptom associations are combinations of symptoms and localisations of those symptoms.

Alternatively or additionally, additional features may be identified from the literature 614 using natural language processing (NLP). Vocabulary/tokens representing clinical terms is identified in medical literature (e.g. on a selection of medical publications from PubMED). The medical literature may be selected to include publications related to the rare disease and a selection of disease with similar symptoms. Natural language processing is used to create a mathematical representation of the clinical terms that is based on the context in which those terms are used in the literature. For example, each term may be represented as an embedding vector in a vector space, with words that occur in a similar context occupying close positions in the vector space, i.e. clinical terms occurring in similar contexts have similar embedding vector representations. An example of a natural language processing algorithm that can be used to generate such embedding vectors is Word2Vec (see, for example, "*Distributed Representations of Words and Phrases and their Compositionality*", Mikolov et al. 2013, Adv. Neural Inf. Process. Syst, Volume 26).

Terms that occur in a similar context to the rare disease and/or its symptoms may be identified as additional features to be included in the training dataset by taking embedding vectors that lie close to (e.g. within a threshold distance of) the embedding vectors for the rare disease/symptoms of the rare disease. A cosine similarity may be used to determine the distance between embedding vectors.

In general, embedding vectors can be determined/generated for every term associated with the rare disease in the literature.

Furthermore, the identified word/term embeddings can be used to generate a vectorisation of each individual in the training dataset. For each individual, a vector representation of that individual can be created, for example by averaging (e.g. taking the mean of) the embedding vectors of the features associated with the individual. In some embodiments, the embedding of the rare disease term may also be subtracted from this representation to create a final vector representation for the individual. Where a control individual has none of the features of the rare disease, they may be represented by a zero vector. Such vector representations may be used as an additional or alternative input to the machine-learned model.

When trained on a corpus composed of biomedical literature, word embeddings enable establishing relationships between concepts such as diseases, symptoms, and treatments. Word embeddings convert concepts into vectors by using the context in which the concepts are mentioned in a body of text. The similarity between two vectors represents how closely they are related. Features can be extracted by computing the distance between symptoms and a given disease and keeping features which are closest (see, for example, "*Learning to Identify Rare Disease Patients from Electronic Health Records*" Colbaugh, et al., 2018, AMIA . . . Annu. Symp. proceedings. AMIA Symp, Volume 2018, pp. 340-347).

Once created, the training dataset is used to train the machine learned model. A testing dataset may be created in substantially the same way as the training dataset, and used to test the performance of the machine learned model after it has been trained. The test dataset may be selected based on the same criteria as the training dataset, but with a different rare disease individual to control individual ratio. The number of control individuals per rare disease individual may be higher in the test dataset than in the training dataset. For example, there may be between 1,000 and 50,000 control individuals per rare disease individual in the testing dataset, e.g. a 1:10,000 rare disease-to-control ratio.

Figure 7:
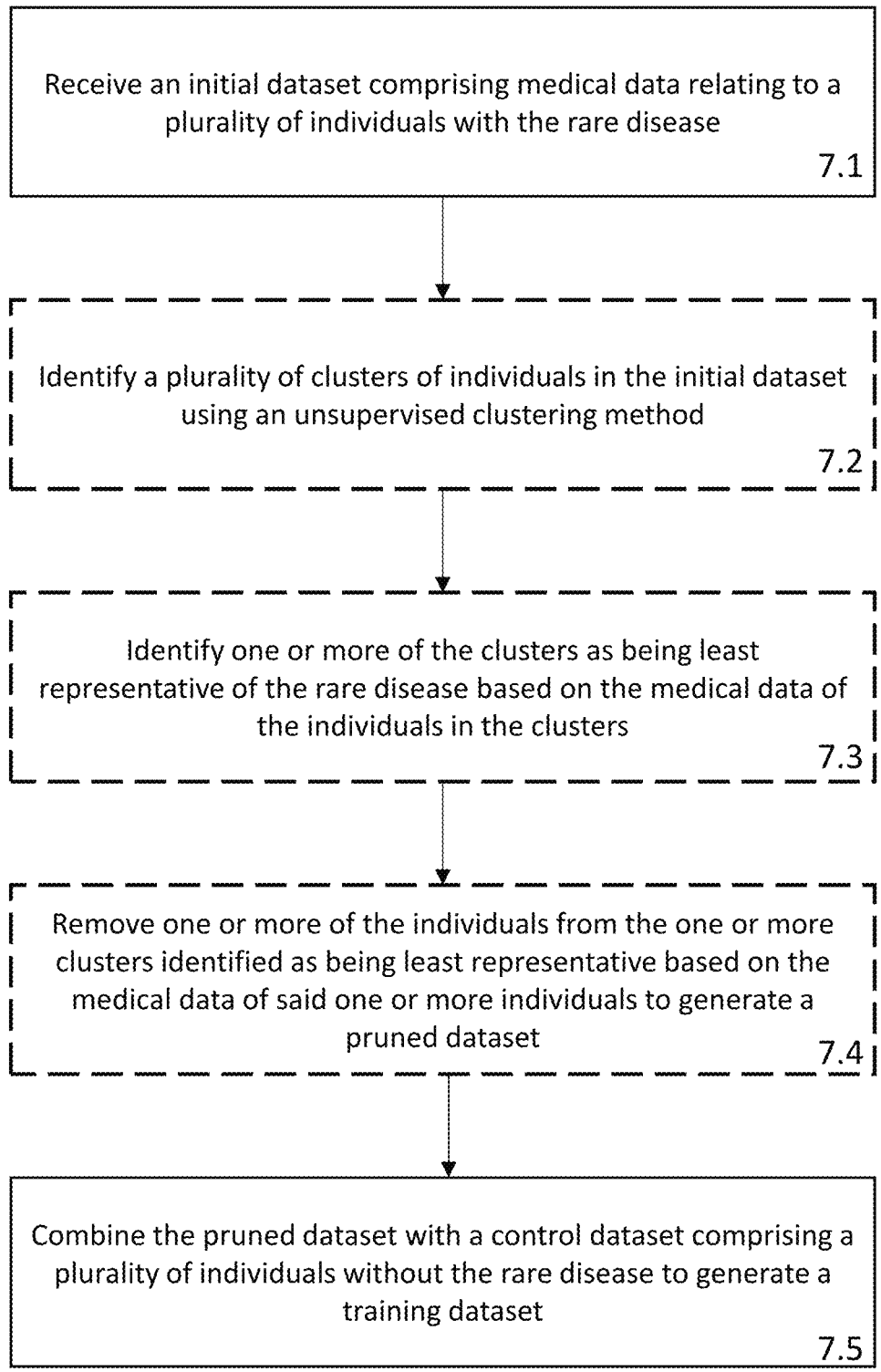
FIG. 7 shows a flowchart of an example method of generating a training dataset for training a machine-learning model to identify individuals with a rare disease.

FIG. 7 shows a flow diagram of an example method of generating a training dataset for use in training a machine-learning model to identify individuals with a rare disease. The method may be performed by a computer.

At operation 7.1, an initial dataset comprising medical data relating to a plurality of individuals with the rare disease is received. The medical data for each individual comprises data indicative of a plurality of symptoms of the rare disease experienced by said individual. The medical data may further comprise one or more of: vital sign data (e.g. BMI, blood pressure, pain scores); lab values (e.g. A1C, eGFR, FEV); biomarkers; medications received by the individual; and/or individual details (e.g. age, gender, smoking status, ethnicity).

At operation 7.2, a plurality of clusters of individuals in the initial dataset are identified using an unsupervised clustering method. The unsupervised clustering algorithm method may be a hierarchical agglomerative clustering algorithm. The clustering algorithm may cluster the dataset into a predetermined number of clusters. The predetermined number may be based on known sub-types of the rare disease, or be a fraction of the known number of symptoms for the rare disease.

At operation 7.3, one or more of the clusters are identified as being least representative of the rare disease based on the medical data of the individuals in the clusters.

Identifying one or more of clusters as being least representative of the rare disease may comprise identifying a representative symptom of the rare disease for each of the plurality of clusters, for example based on the most common symptom or set of symptoms experienced by individuals in each cluster and/or demographic properties of the individuals in each cluster. The representative symptom for each cluster may be compared to a predefined set of known symptoms of the rare disease, the predefined set of known symptoms comprising a set of more representative symptoms and a set of least representative symptoms. A cluster may be identified as being least representative of the rare disease if the representative symptom of the cluster is in the set of least representative symptoms.

At operation 7.4, one or more of the individuals are removed from the one or more clusters identified as being least representative based on the medical data of said one or more individuals to create a pruned dataset. For each individual in the clusters identified as being least representative, this may comprise determining whether medical data associated with the individual satisfies a threshold condition and removing the individual from the identified clusters if the threshold condition is not satisfied. The threshold condition may be based on symptoms of the rare disease, for example having at least a threshold number of symptoms of the rare disease. The threshold condition may alternatively or additionally comprise having at least one symptom of the rare disease in a characteristic subset of symptoms of the rare disease.

At operation 7.5, the pruned dataset is combined with a control dataset comprising a plurality of individuals without the rare disease to generate the training dataset. The control dataset may comprise individuals without the rare disease having at least a threshold number of symptoms of the rare disease. Combining the pruned dataset with a control dataset may comprise matching a plurality of individuals in the control dataset to each individual in the pruned dataset at a predefined ratio, e.g. ten control individuals for each RD individual. The matching may be based on one or more demographic properties of the individuals in the pruned dataset.

In some embodiments, operations 7.2-7.4 are not performed, i.e. the "pruned" dataset is just the initial dataset, potentially augmented with additional data for rare disease features. In some embodiments, the initial dataset may be clustered to identify features, but not pruned based on those features, i.e. operation 7.2 is performed, but not operations 7.3 and 7.4.

The method may, in some embodiments, further comprise one or more data augmentation operations following the merging of the control dataset and pruned dataset. The data augmentation operations identify one or more potential indicators of the rare disease and incorporate them into the training dataset as labels. The augmentation may comprise comparing medical data associated with individuals in the pruned dataset to medical data associated with individuals in the control dataset to identify one or more potential symptoms of the rare disease, and augmenting the training dataset with the one or more potential symptoms of the rare disease. Alternatively or additionally, the data augmentation may comprise extracting, using natural language processing, one or more potential symptoms of the rare disease from literature relating to the rare disease, and augmenting the training dataset with the one or more potential symptoms of the rare disease.

In some embodiments, the method comprises generating, from a corpus of medical literature associated with the rare disease and using natural language processing, an embedding vector for each of a plurality of terms associated with the rare disease. In some embodiments, an embedding vector for each of a plurality of terms in the corpus of medical literature is generated using a natural language processing algorithm, such as Word2Vec. Each of the embedding vectors may be normalised.

These embedding vectors may then be compared to embedding vectors of one or more predefined terms known to be associated with the rare disease, such as the embedding vector for the rare disease itself and/or its known symptoms, using a distance metric. The embedding vectors associated with the predefined terms are generated using the same method as the embedding vectors from the corpus of medical literature. The distance metric may be any metric form measuring a difference between two vectors, such as a dot product between (normalised) embedding vectors or a cosine similarity. Embedding vectors for terms in the corpus of medical literature are discarded if a distance between said embedding vector and an embedding vector of a predefined term known to be associated with the rare disease is greater than a threshold value in order to generate a set of embedding vectors for terms associated with the rare disease.

Once the training set has been generated, the method may further comprise generating, for each individual in the training dataset, an embedding vector representing the individual based on features associated with the individual and the embedding vectors for the plurality of terms associated with the rare disease. Generating the embedding vector representing an individual may comprise identifying one or more embedding vectors for terms associated with rare disease that correspond to features of the rare disease experienced by the individual and averaging the identified embedding vectors for terms associated with rare disease to generate the embedding vector representing the individual. In other words, the embedding of an individual is the average over the embedding vectors of features associated with that individual. In some embodiments, the embedding vector for the rare disease term itself is subtracted from the embedding vectors for the individuals, i.e. the embedding vector representing an individual represents a difference between the embedding vector of the rare disease term and the average embedding vector of the features associated with the individual.

The training dataset may then be used to train a machine-learned model to identify individuals with the rare disease. The machine-learned model is trained using supervised learning techniques. During the training of the model, medical data associated with an individual is input into the model and a proposed classification obtained from the model indicative of whether the individual has the rare disease. In some implementations, the medical data input into the machine-learned model comprises an embedding vector associated with the individual. The proposed classification is compared to the known classification for the individual. Parameters of the model are updated based on the comparison.

In some embodiments, a subset of the medical data associated with an individual may be input into the model. For example, for individuals with the rare disease, only medical data prior to the diagnoses of that individual may be input into the model, e.g. up to the time of diagnoses, or up to some predefined time before diagnoses. This can reduce the bias associated with post-diagnoses symptom collection.

Once trained, the machine-learned model can be used to identify individuals who potentially have the rare disease. Medical data associated with an individual is input into the model. In some implementations, the medical data input into the machine-learned model comprises an embedding vector associated with the individual. The model processes the input medical data to generate data indicative of whether the individual associated with the medical data as the disease, e.g. a binary classification of whether the individual has the disease or a probability that the individual has the disease. The data indicative of whether the individual associated with the medical data has the disease is output from the model.

Figure 8:
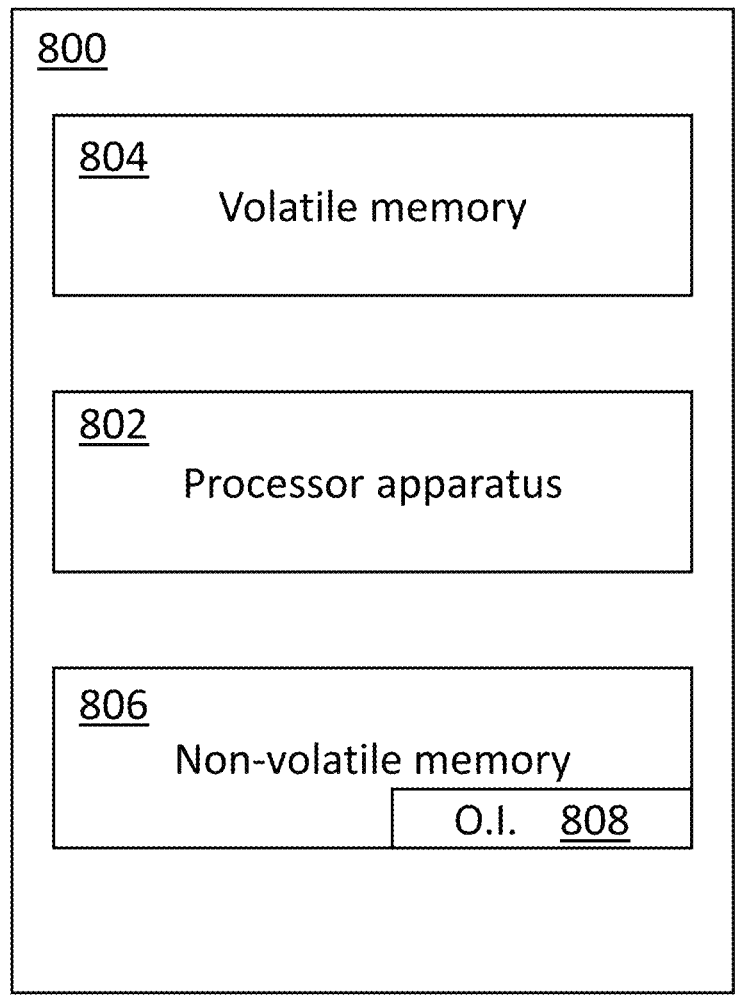
FIG. 8 shows an example of a computing system/apparatus for performing the methods described herein.

FIG. 8 shows a schematic example of a system/apparatus for performing any of the methods described herein. The system/apparatus shown is an example of a computing device. It will be appreciated by the skilled person that other types of computing devices/systems may alternatively be used to implement the methods described herein, such as a distributed computing system.

The apparatus (or system) 800 comprises one or more processors 802. The one or more processors control operation of other components of the system/apparatus 800. The one or more processors 802 may, for example, comprise a general-purpose processor. The one or more processors 802 may be a single core device or a multiple core device. The one or more processors 802 may comprise a Central Processing Unit (CPU) or a graphical processing unit (GPU). Alternatively, the one or more processors 802 may comprise specialised processing hardware, for instance a RISC processor or programmable hardware with embedded firmware. Multiple processors may be included.

The system/apparatus comprises a working or volatile memory 804. The one or more processors may access the volatile memory 804 in order to process data and may control the storage of data in memory. The volatile memory 804 may comprise RAM of any type, for example, Static RAM (SRAM), Dynamic RAM (DRAM), or it may comprise Flash memory, such as an SD-Card.

The system/apparatus comprises a non-volatile memory 806. The non-volatile memory 806 stores a set of operation instructions 808 for controlling the operation of the processors 802 in the form of computer readable instructions. The non-volatile memory 806 may be a memory of any kind such as a Read Only Memory (ROM), a Flash memory or a magnetic drive memory.

The one or more processors 802 are configured to execute operating instructions 808 to cause the system/apparatus to perform any of the methods described herein. The operating instructions 808 may comprise code (i.e. drivers) relating to the hardware components of the system/apparatus 800, as well as code relating to the basic operation of the system/apparatus 800. Generally speaking, the one or more processors 802 execute one or more instructions of the operating instructions 808, which are stored permanently or semi-permanently in the non-volatile memory 806, using the volatile memory 804 to store temporarily data generated during execution of said operating instructions 808.

Implementations of the methods described herein may be realised as in digital electronic circuitry, integrated circuitry, specially designed ASICs (application specific integrated circuits), computer hardware, firmware, software, and/or combinations thereof. These may include computer program products (such as software stored on e.g. magnetic discs, optical disks, memory, Programmable Logic Devices) comprising computer readable instructions that, when executed by a computer, such as that described in relation to FIG. 8, cause the computer to perform one or more of the methods described herein.

Any system feature as described herein may also be provided as a method feature, and vice versa. As used herein, means plus function features may be expressed alternatively in terms of their corresponding structure. In particular, method aspects may be applied to system aspects, and vice versa.

Furthermore, any, some and/or all features in one aspect can be applied to any, some and/or all features in any other aspect, in any appropriate combination. It should also be appreciated that particular combinations of the various features described and defined in any aspects of the invention can be implemented and/or supplied and/or used independently.

Although several embodiments have been shown and described, it would be appreciated by those skilled in the art that changes may be made in these embodiments without departing from the principles of this disclosure, the scope of which is defined in the claims and their equivalents.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases.

Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(w-carboxyheptadecanoyl)-des(B30) human insulin and B29-N-(w-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A computer implemented method of generating a training dataset for training a machine learning model to identify individuals with a rare disease, the method comprising:
generating a respective first embedding vector for each of a plurality of terms associated with the rare disease, wherein the plurality of terms are obtained by using natural language processing on medical literature associated with the rare disease;
receiving an initial dataset comprising respective medical data associated with a plurality of individuals with the rare disease, the respective medical data for each individual comprising data indicative of a plurality of features of the rare disease experienced by the individual;
combining the initial dataset with a control dataset comprising respective medical data associated with a plurality of individuals without the rare disease to generate a combined dataset; and
generating, for each individual in the combined dataset, a second embedding vector that represents the individual based on (i) features associated with the individual and (ii) the first embedding vectors for the plurality of terms associated with the rare disease, wherein the second embedding vectors form the training dataset, wherein generating the second embedding vector representing an individual comprises:
identifying one or more first embedding vectors that correspond to particular terms associated with features of the rare disease experienced by the individual;
averaging the identified first embedding vectors to generate an average embedding vector for the individual; and
modifying the average embedding vector representing the individual using an embedding vector representing a name of the rare disease to generate the second embedding vector, the modifying comprising subtracting the embedding vector representing a name of the rare disease from the average embedding vector representing the individual; and
training the machine learning model on the training dataset comprising the second embedding vectors using a machine learning training technique to determine trained values of a set of model parameters of the machine learning model.

2. The method of claim 1, wherein generating the respective first embedding vector for each of the plurality of terms comprises:
determining a respective distance metric for each first embedding vector by comparing the first embedding vector to predefined embedding vectors of one or more predefined terms known to be associated with the rare disease; and
discarding, from the first embedding vectors, a particular first embedding vector that has a distance metric from a predefined embedding vector greater than a threshold value.

3. The method of claim 1, further comprising:
identifying, by using an unsupervised clustering method, a plurality of clusters of individuals whose medical data is in the initial dataset;
identifying, from among the clusters, one or more least-representative clusters as being least representative of the rare disease based on the medical data of the individuals in the clusters; and
removing, from the initial dataset and prior to combining the initial dataset with the control dataset, medical data of one or more individuals in the one or more least-representative clusters based on the medical data of the one or more individuals.

4. The method of claim 3, wherein identifying the one or more least-representative clusters comprises:
identifying a respective representative symptom of the rare disease for each of the plurality of clusters;
comparing the respective representative symptom for each cluster to a predefined set of specific symptoms of the rare disease, the predefined set of specific symptoms comprising a predefined set of more representative symptoms and a predefined set of least representative symptoms; and
identifying a cluster as being one of the least-representative clusters in response to determining that the representative symptom of the cluster is in the predefined set of least representative symptoms.

5. The method of claim 3, wherein removing the medical data of the one or more of the individuals comprises:
for each individual in the least-representative clusters: determining whether medical data associated with the individual satisfies a threshold condition, the threshold condition being defined based on symptoms of the rare disease; and in response to determining that the threshold condition is not satisfied, removing the individual from the plurality of clusters.

6. The method of claim 3, wherein identifying the plurality of clusters of individuals in the initial dataset comprises using a hierarchical agglomerative clustering to cluster the initial dataset into a predetermined number of clusters.

7. The method of claim 1, further comprising:
comparing the medical data in the initial dataset to the medical data in the control dataset to identify one or more potential symptoms of the rare disease; and
augmenting the training dataset with the one or more potential symptoms of the rare disease.

8. The method of claim 1, wherein the control dataset comprises medical data of individuals without the rare disease having at least a threshold number of symptoms of the rare disease.

9. The method of claim 1, wherein combining the initial dataset with the control dataset comprises matching a plurality of individuals with medical data in the control dataset to each individual with medical data in the initial dataset at a predefined ratio, the matching being based on one or more demographic properties of the individuals.

10. The method of claim 1, wherein training the machine learning model on the training dataset comprising the second embedding vectors using the machine learning training technique to determine trained values of the set of model parameters of the machine learning model comprises:
using the training dataset to train the machine learning model to classify a particular individual as having the rare disease by using a supervised learning technique, wherein the machine learning model takes as input data comprising a second embedding vector representing the particular individual.

11. The method of claim 10, wherein the machine learning model is trained on a subset of data in the training dataset, the subset comprising, for each individual with medical data in the training dataset with the rare disease, medical data collected prior to the individual being diagnosed with the rare disease.

12. The method of claim 1, further comprising diagnosing that a particular individual has the rare disease by:
inputting, into the machine learning model, medical data associated with the particular individual, the medical data being in form of a particular embedding vector representing medical records of the particular individual;
processing, using the machine learning model, the input medical data to generate data indicative of whether the particular individual has the disease; and
outputting, from the machine learning model, the data indicative of whether the particular individual has the disease.

13. A system comprising one or more processors and a memory, the memory comprising computer readable code that, when executed by the one or more processors, causes the system to perform operations for generating a training dataset for training a machine learning model to identify individuals with a rare disease, the operations comprising:
generating a respective first embedding vector for each of a plurality of terms associated with the rare disease, wherein the plurality of terms are obtained by using natural language processing on medical literature associated with the rare disease;
receiving an initial dataset comprising respective medical data associated with a plurality of individuals with the rare disease, the respective medical data for each individual comprising data indicative of a plurality of features of the rare disease experienced by the individual;
combining the initial dataset with a control dataset comprising respective medical data associated with a plurality of individuals without the rare disease to generate a combined dataset; and
generating, for each individual in the combined dataset, a second embedding vector that represents the individual based on (i) features associated with the individual and (ii) the first embedding vectors for the plurality of terms associated with the rare disease, wherein the second embedding vectors form the training dataset, wherein generating the second embedding vector representing an individual comprises:
identifying one or more first embedding vectors that correspond to particular terms associated with features of the rare disease experienced by the individual;
averaging the identified first embedding vectors to generate an average embedding vector for the individual; and
modifying the average embedding vector representing the individual using an embedding vector representing a name of the rare disease to generate the second embedding vector, the modifying comprising subtracting the embedding vector representing a name of the rare disease from the average embedding vector representing the individual; and
training the machine learning model on the training dataset comprising the second embedding vectors using a machine learning training technique to determine trained values of a set of model parameters of the machine learning model.

14. The system of claim 13, wherein training the machine learning model on the training dataset comprising the second embedding vectors using the machine learning training technique to determine trained values of the set of model parameters of the machine learning model comprises:
using the training dataset to train the machine learning model to classify an individual as having a rare disease by using a supervised learning technique, wherein the machine learning model takes as input data comprising a second embedding vector representing an individual.

15. A non-transitory, computer-readable medium storing one or more instructions executable by a computer system to perform operations for generating a training dataset for training a machine learning model to identify individuals with a rare disease, the operations comprising:
generating a respective first embedding vector for each of a plurality of terms associated with the rare disease, wherein the plurality of terms are obtained by using natural language processing on medical literature associated with the rare disease;
receiving an initial dataset comprising respective medical data associated with a plurality of individuals with the rare disease, the respective medical data for each individual comprising data indicative of a plurality of features of the rare disease experienced by the individual;

combining the initial dataset with a control dataset comprising respective medical data associated with a plurality of individuals without the rare disease to generate a combined dataset; and generating, for each individual in the combined dataset, a second embedding vector that represents the individual based on (i) features associated with the individual and (ii) the first embedding vectors for the plurality of terms associated with the rare disease, wherein the second embedding vectors form the training dataset, wherein generating the second embedding vector representing an individual comprises:

identifying one or more first embedding vectors that correspond to particular terms associated with features of the rare disease experienced by the individual;

averaging the identified first embedding vectors to generate an average embedding vector for the individual; and modifying the average embedding vector representing the individual using an embedding vector representing a name of the rare disease to generate the second embedding vector, the modifying comprising subtracting the embedding vector representing a name of the rare disease from the average embedding vector representing the individual; and training the machine learning model on the training dataset comprising the second embedding vectors using a machine learning training technique to determine trained values of a set of model parameters of the machine learning model.

16. The non-transitory, computer-readable medium of claim 15, wherein training the machine learning model on the training dataset comprising the second embedding vectors using the machine learning training technique to determine trained values of the set of model parameters of the machine learning model comprises:

using the training dataset to train the machine learning model to classify an individual as having a rare disease by using a supervised learning technique, wherein the machine learning model takes as input data comprising a second embedding vector representing an individual.

17. The non-transitory, computer-readable medium of claim 15, wherein the operations further comprise:

identifying, by using an unsupervised clustering process, a plurality of clusters of individuals whose medical data is in the initial dataset;

identifying, from among the clusters, one or more least-representative clusters as being least representative of the rare disease based on the medical data of the individuals in the clusters; and removing, from the initial dataset and prior to combining the initial dataset with the control dataset, medical data of one or more individuals in the one or more least-representative clusters based on the medical data of the one or more individuals.

18. The non-transitory, computer-readable medium of claim 17, wherein identifying the one or more least-representative clusters comprises:

identifying a respective representative symptom of the rare disease for each of the plurality of clusters;

comparing the respective representative symptom for each cluster to a predefined set of specific symptoms of the rare disease, the predefined set of specific symptoms comprising a predefined set of more representative symptoms and a predefined set of least representative symptoms; and identifying a cluster as being one of the least-representative clusters in response to determining that the representative symptom of the cluster is in the predefined set of least representative symptoms.

19. The non-transitory, computer-readable medium of claim 17, wherein removing the medical data of the one or more of the individuals comprises:

for each individual in the least-representative clusters:

determining whether medical data associated with the individual satisfies a threshold condition, the threshold condition being defined based on symptoms of the rare disease; and in response to determining that he threshold condition is not satisfied, removing the individual from the plurality of clusters.

20. The non-transitory, computer-readable medium of claim 17, wherein generating the respective first embedding vector for each of the plurality of terms comprises:

determining a respective distance metric for each first embedding vector by comparing the first embedding vector to predefined embedding vectors of one or more predefined terms known to be associated with the rare disease; and discarding, from the first embedding vectors, a particular first embedding vector that has a distance metric from a predefined embedding vector greater than a threshold value.

* * * * *

UNITED STATES PATENT AND TRADEMARK OFFICE
CERTIFICATE OF CORRECTION

| | | |
|---|---|---|
| PATENT NO. | : 12,136,492 B2 | Page 1 of 1 |
| APPLICATION NO. | : 17/448507 | |
| DATED | : November 5, 2024 | |
| INVENTOR(S) | : Cliona Marie Molony and Alexandra Dumitriu | |

It is certified that error appears in the above-identified patent and that said Letters Patent is hereby corrected as shown below:

On the Title Page

Column 2, Line 6, item (57), under "ABSTRACT", delete "disease. the" and insert -- disease. The --

In the Claims

Column 26, Line 35, Claim 19, delete "that he" and insert -- that the --

Signed and Sealed this
Twenty-second Day of July, 2025

Coke Morgan Stewart
*Acting Director of the United States Patent and Trademark Office*